US012747819B2

(12) United States Patent
Dash et al.

(10) Patent No.: US 12,747,819 B2
(45) Date of Patent: Sep. 29, 2026

(54) CLAMP ASSEMBLIES FOR CLAMPING TUBING AND CONTROLLING FLUID FLOW

(71) Applicant: CORNING INCORPORATED, Corning, NY (US)

(72) Inventors: Manas Ranjan Dash, Wayland, MA (US); Gregory Roger Martin, Acton, ME (US); Andreas Alfred Weiss, Nashua, NH (US)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 18/878,291

(22) PCT Filed: Jun. 27, 2023

(86) PCT No.: PCT/US2023/026287

§ 371 (c)(1),
(2) Date: Dec. 23, 2024

(87) PCT Pub. No.: WO2024/015209

PCT Pub. Date: Jan. 18, 2024

(65) Prior Publication Data

US 2025/0243959 A1 Jul. 31, 2025

Related U.S. Application Data

(60) Provisional application No. 63/388,458, filed on Jul. 12, 2022.

(51) Int. Cl.
*F16K 7/06* (2006.01)
*A61M 39/28* (2006.01)
*F16L 55/10* (2006.01)

(52) U.S. Cl.
CPC ........... *F16L 55/10* (2013.01); *A61M 39/284* (2013.01); *F16K 7/063* (2013.01)

(58) Field of Classification Search
CPC ........ F16L 55/10; F16K 7/063; A61M 39/284
See application file for complete search history.

(56) References Cited

U.S. PATENT DOCUMENTS 4,676,476 A * 6/1987 Herrli ................. A61M 39/284 251/9
7,434,779 B2 10/2008 Werth
11,116,288 B2 * 9/2021 Taylor .................. A44B 11/125
2006/0169934 A1 * 8/2006 Werth ..................... F16K 7/063 251/9
2018/0104467 A1 * 4/2018 Kato ..................... A61M 39/28

* cited by examiner

*Primary Examiner* — Kelsey E Cary
(74) *Attorney, Agent, or Firm* — Chandra J. Duncan

(57) ABSTRACT

A clamp assembly for clamping flexible tubing includes a base member including a pair of sidewalls and a bottom that extends between the sidewalls. At least one of the sidewalls includes a clamp latching feature that extends inward from an inner surface of the at least one of the sidewalls. A locking lever is located between the sidewalls and is pivotally connected to the sidewalls at a pivot location such that the locking lever pivots relative to the base member. The locking lever includes a lever catch feature configured to cooperatively mate with the clamp latching feature.

19 Claims, 6 Drawing Sheets

CLAMP ASSEMBLIES FOR CLAMPING TUBING AND CONTROLLING FLUID FLOW

CROSS-REFERENCE TO RELATED APPLICATIONS

This is a national stage application under 35 U.S.C. § 371 of International Application No. PCT/US2023/026287, filed Jun. 27, 2023, which claims the benefit of priority under 35 U.S.C. § 119 of U.S. Provisional Application Ser. No. 63/388,458 filed on Jul. 12, 2022, the content of which are relied upon and incorporated herein by reference in their entirety.

BACKGROUND

Field

The present specification generally relates to clamp assemblies and, more particularly, to clamp assemblies for clamping tubing and controlling fluid flow through the tubing.

Technical Background

Many laboratory systems utilize flexible tubing to direct or transfer fluids from one system to another system. One such system that utilizes flexible tubing is Corning's HYPERStack™. The HYPERStack™ system includes multiple modules formed of individual stackette layers that can be interconnected by flexible tubes that connect to tube connectors. The modules are interconnected for filling and emptying the HYPERStack™ system. Valves and other devices, such as clamps, may be used to control fluid flow into and out of the HYPERStack™ system using a flexible tube. For example, during filling and emptying of the HYPERStack™, it may be desirable to slow or stop fluid flow into and out of the system through the tube.

Accordingly, a need exists for a clamp assembly that is suitable for clamping flexible tubing to control fluid flow through the tubing.

SUMMARY

According to one embodiment, a clamp assembly for clamping flexible tubing includes a base member including a pair of sidewalls and a bottom that extends between the sidewalls. At least one of the sidewalls includes a clamp latching feature that extends inward from an inner surface of the at least one of the sidewalls. A locking lever is located between the sidewalls and is pivotally connected to the sidewalls at a pivot location such that the locking lever pivots relative to the base member. The locking lever includes a lever catch feature configured to cooperatively mate with the clamp latching feature.

According to another embodiment, a clamp assembly for clamping flexible tubing includes a base member comprising a pair of sidewalls and a bottom that extends between the sidewalls At least one of the sidewalls includes a clamp latching feature. A locking lever is located between the sidewalls and is pivotally connected to the sidewalls at a pivot location such that the locking lever pivots relative to the base member. The locking lever includes a lever catch feature configured to cooperatively mate with the clamp latching feature. A de-pinching feature is configured to move inward and impinge upon tubing located in the base member.

Additional features and advantages of the clamp assemblies and methods will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Embodiments described herein are generally directed to clamp assemblies that are used to clamp down on flexible tubing thereby reducing an inner diameter of the tubing to reduce or stop flow through the tubing. The clamp assembly includes a base member that includes a pair of sidewalls and a bottom that extends between the sidewalls. At least one of the sidewalls has at least two clamp latching features spaced-apart from each other along an inner surface of the at least one of the sidewalls such that the clamp latching features are different distances from the bottom. A locking lever is pivotally connected to the sidewalls at a pivot location such that the locking lever pivots relative to the base member. The locking lever includes a lever catch feature that is configured to cooperatively mate with the clamp latching features. The lever catch features mates with one of the clamp latching features at a first angular position relative to the base member to lock the locking lever at the first angular position and mates with another of the clamp latching features at a different, second angular position relative to the base member to lock the locking lever at the second angular position. At least one of the sidewalls may include a tubing de-pinch feature that can move inward toward the other of the sidewalls to impinge on and apply pressure against the tubing.

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms “a”, “an”, and “the” encompass embodiments having plural referents, unless the content clearly dictates otherwise. As used in this specification and the appended claims, the term “or” is generally employed in its sense including “and/or” unless the content clearly dictates otherwise.

As used herein, “have”, “having”, “include”, “including”, “comprise”, “comprising” or the like are used in their open ended sense, and generally mean “including, but not limited to.”

Figure 1:
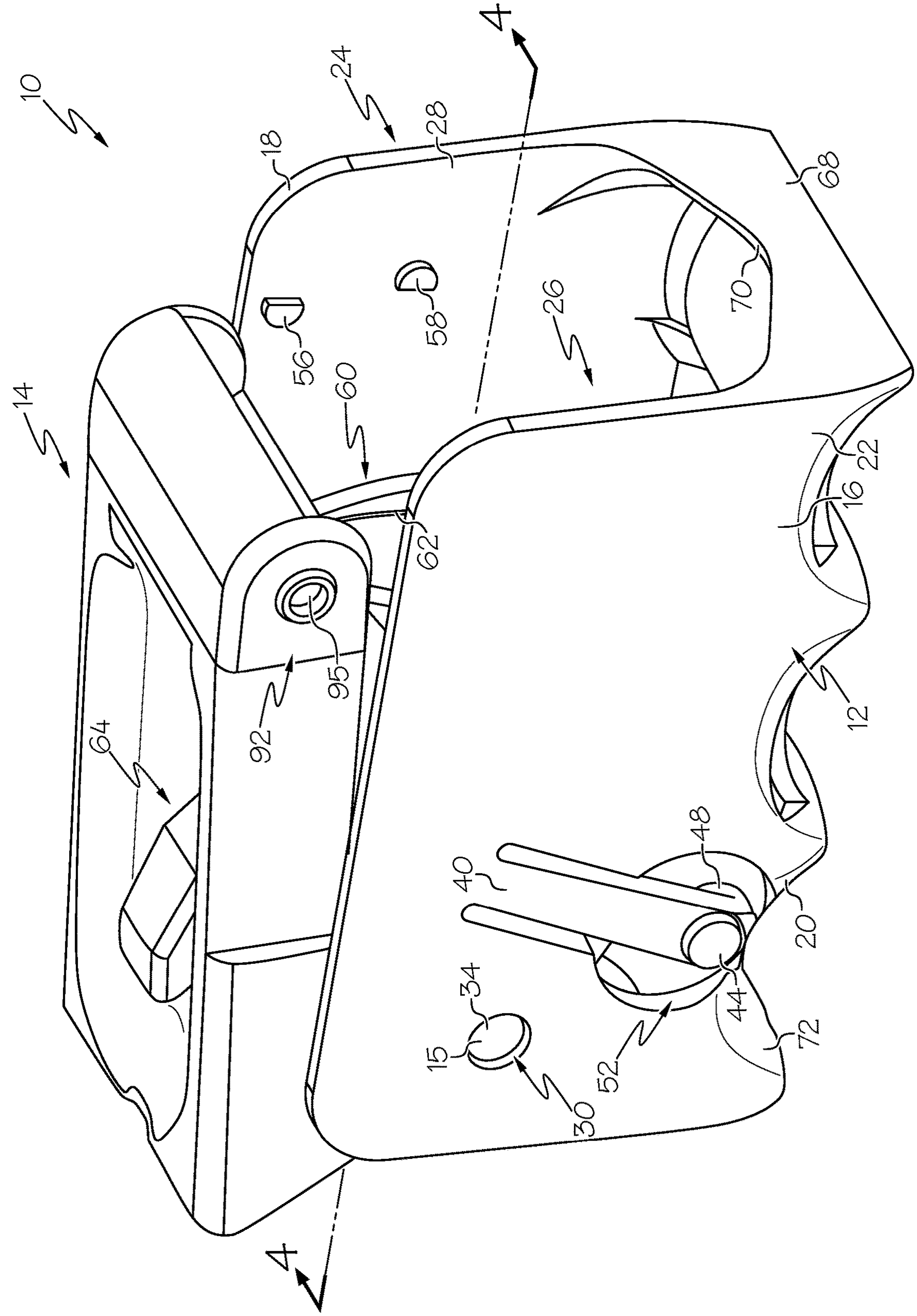
FIG. 1 is a side perspective view of a clamp assembly for clamping and pinching flexible tubing in an open configuration, according to one or more embodiments shown and described herein.

Referring to FIG. 1, a clamp assembly 10 includes a base member 12 and a locking lever 14. The base member 12 and the locking lever 14 may be separate components that are connected together at a pivot location 15 such that the locking lever 14 can pivot relative to the base member 12. It should be noted that features of the clamp assembly 10 including the base member 12 and the locking lever 14 may be the same on opposite sides of a geometric centerline of the clamp assembly 10.

Figure 2:
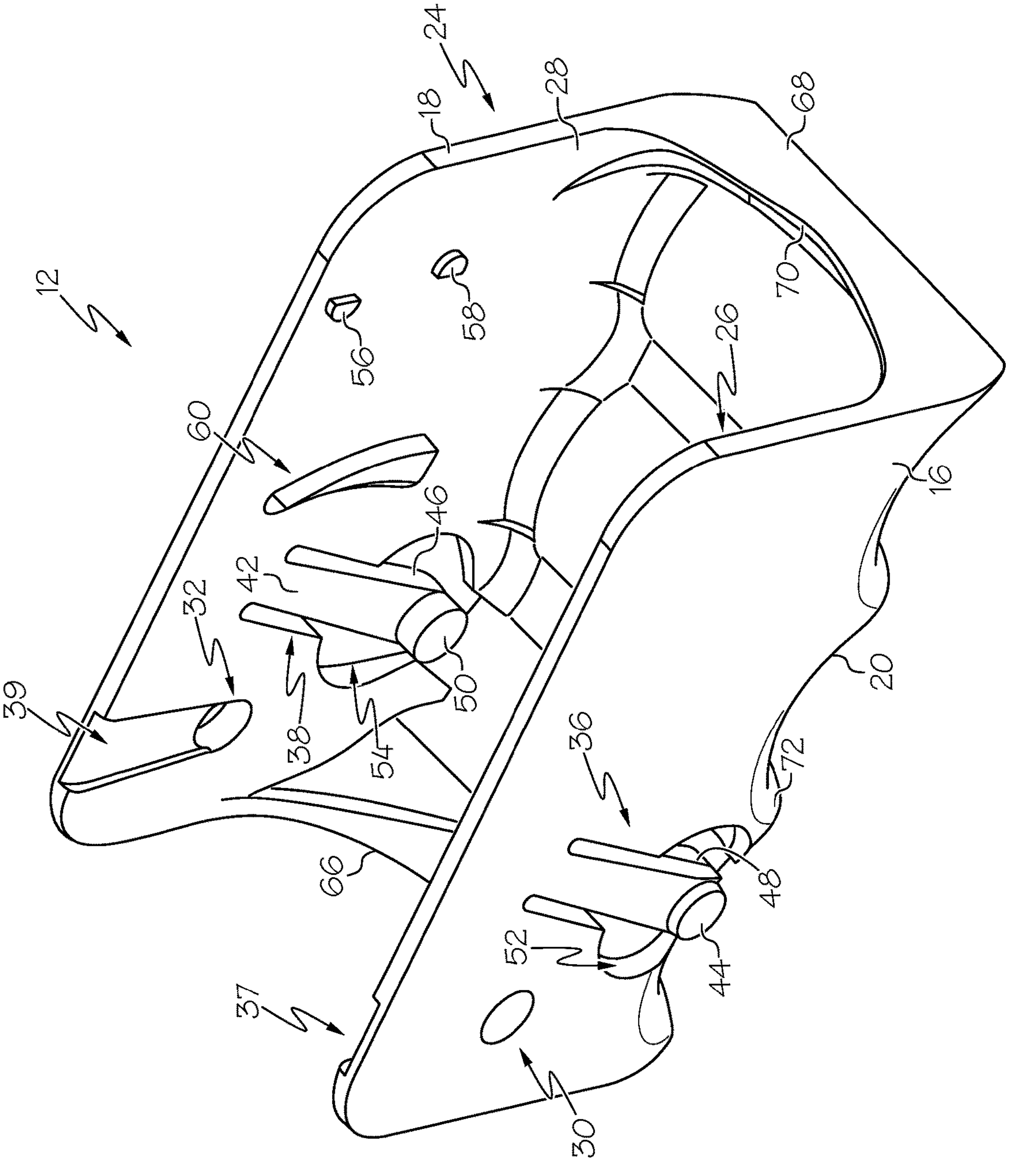
FIG. 2 is a top perspective view of a base member of the clamp assembly of FIG. 1 in isolation, according to one or more embodiments shown and described herein.

Referring also to FIG. 2, the base member 12 includes opposing sidewalls 16 and 18 and a bottom 20 that extends between the sidewalls 16 and 18 forming a U-shape in section. Each sidewall 16, 18 includes an outer surface 22, 24 and an inner surface 26, 28. Openings 30 and 32 are provided through the sidewalls 16, 18 at the pivot location 15. The openings 30 and 32 are sized and located to receive pivot projections 34 (FIG. 1) of the locking lever 14. In some embodiments, guide recesses 37 and 39 (FIG. 2) may be provided that intersect the openings 30 and 32 to guide and facilitate insertion of the pivot projections 34 into the openings 30 and 32.

Both sidewalls 16, 18 may include de-pinch features 36 and 38 that are formed as cantilevered tabs that are connected to the sidewalls 16, 18 at a mounted end 40 and 42 and extend to an opposite, free end 44 and 46. At the free ends 44 and 46 are projections 48 and 50 that extend inward toward one another. As used herein, the term “inward” refers to toward the geometric centerline of the base member 12. The de-pinch features 36 and 38 are configured to resiliently flex such that the projections 48 and 50 can be manually moved toward one another for a tube de-pinching operation. The de-pinch features 36 and 38 may return to their initial, unflexed positions when they are released. Finger-receiving openings 52 and 54 may be provided around the free ends 44 and 46 that are sized to receive fingers pushing the free ends 44 and 46 and facilitate movement of the de-pinch features 36 and 38. The de-pinch features 36 and 38 are configured to impinge upon sides of tubing passing through the base member 12 to help return the tubing nearer to its original inner diameter and increase flowrate therethrough.

Each sidewall 16, 18 further includes clamp latching features 56 and 58. Only clamp latching features 56, 58 of the sidewall 18 can be seen in FIGS. 1 and 2, but the other sidewall 16 may include the clamp latching features 56, 58 forming opposing clamp latching features 56, 58. The clamp latching features 56 and 58 may be formed as inner wall posts that protrude outward from the inner surfaces 26 and 28 of the sidewalls 16 and 18 thereby providing point-type latching locations on an interior of the sidewalls 16, 18. As can be seen, the clamp latching features 56 and 58 are spaced-apart from each other along the inner surfaces 26 and 28 such that the clamp latching features 56 and 58 are different distances from the bottom 20. The clamp latching features 56 are farthest from the bottom 20 and provide a first locking position for the locking lever 14 that is farthest from the bottom 20. The clamp latching features 58 are closest to the bottom 20 and provide a second locking position for the locking lever 14 that is closest to the bottom 20.

Each sidewall 16, 18 also includes a wall separation feature 60. Only wall separation feature 60 of the sidewall 18 can be seen in FIG. 2, but the other sidewall 16 may include the wall separation feature 60 forming opposing wall separation features 60. Each wall separation feature 60 includes a cam surface 62 against which a follower separation arm 64 (FIG. 3) travels. As will be described in greater detail, the cam surface 62 and follower separation arm 64 can cooperate to provide greater separation between the sidewalls 16 and 18 when it is desired to separate the locking lever 14 from the clamp latching features 56 and 58.

The base member 12 further includes end walls 66 and 68. The end walls 66 and 68 may be part of the bottom 20 or they may extend outward from the bottom 20. The end walls 66 and 68 are located at locations of ingress and egress for the tubing as the tubing enters/exits the base member 12. The end walls 66 and 68 are tapered in thickness from each of the sidewalls 16, 18 to the centerline of the base member 12. In this regard, the end walls 66 and 68 have a height that is reduced at their center 70 compared to at the sidewalls 16, 18. Such a tapered arrangement can allow added space for tubing hardware to pass through, if needed. The bottom 20 may also be provided with undulations 72 that are peaks and valleys to fit a user’s fingers and can provide comfort and stability during a clamping operation.

Figure 3:
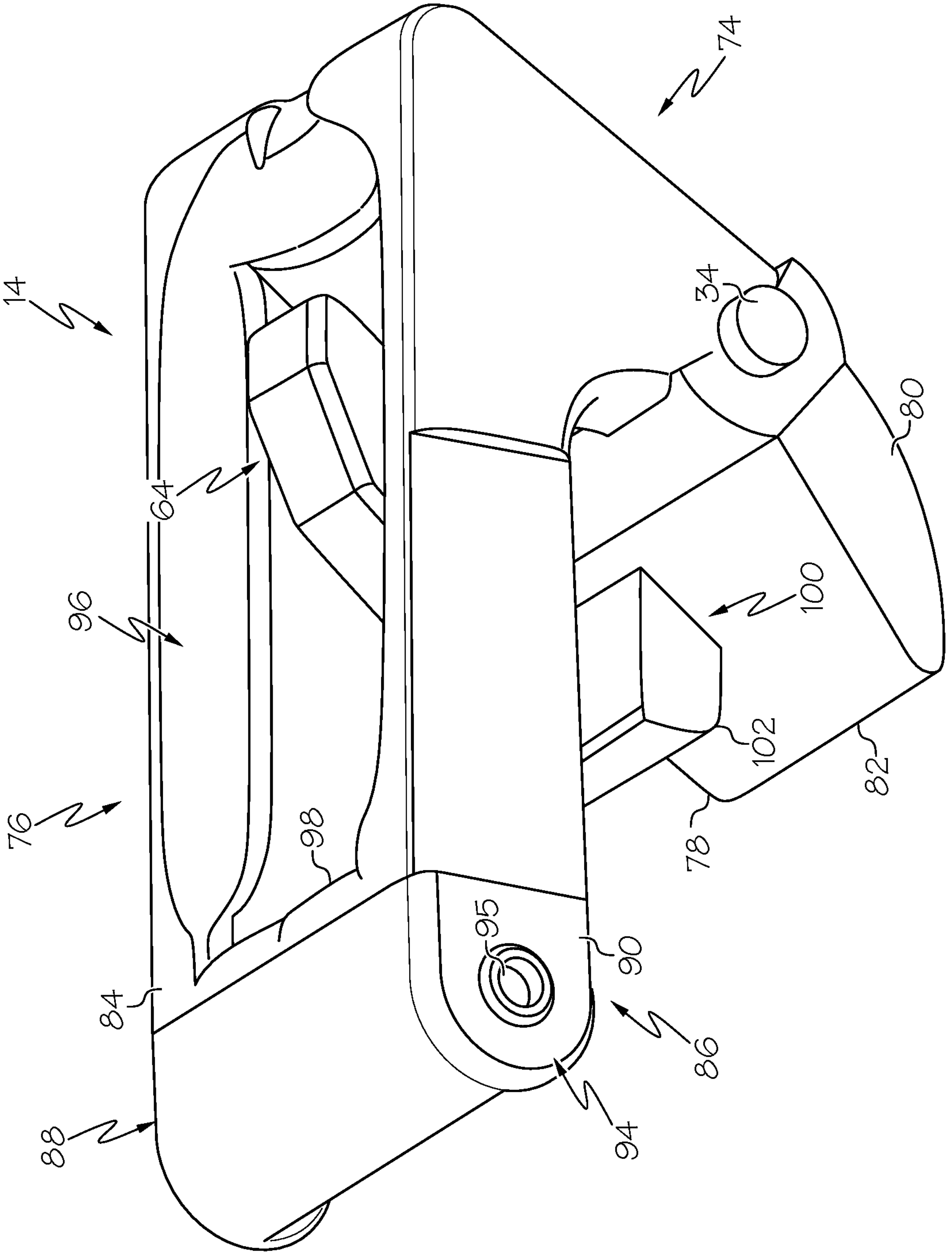
FIG. 3 is a top perspective view of a locking lever of the clamp assembly of FIG. 1 in isolation, according to one or more embodiments shown and described herein.

Referring to FIG. 3, the locking lever 14 is illustrated in isolation and includes a pinching portion 74 and a lever portion 76. The lever portion 76 and the pinching portion 74 extend at an angle to one another to form a somewhat V-shape. The pinching portion 74 includes opposite sides 78 and 80 and a pinching edge 82 that extends between the sides 78 and 80. The pivot projections 34 are located at each side 78 and 80 and are sized to be received by the openings 30 and 32 providing the pivot location 15.

The lever portion 76 extends outward from the pinching portion 74 at an oblique angle and includes an outward facing side 84 that faces away from the bottom 20 of the base member 12 and an inner facing side 86 that faces the bottom 20 of the base member 12. The lever portion 76 has opposite sides 88 and 90 that each include a latch catch feature 92 and 94 (FIG. 1). The latch catch features 92 each have a recessed area 95 that is sized and located to receive the clamp latching features 56 and 58 as the locking lever 14 rotates.

The lever portion 76 further includes an access opening 96 that extends through the lever portion 76. The access opening 96 exposes the follower separation arm 64. The follower separation arm 64 is cantilevered to the lever portion 76 at a mounted end 98 so that when the follower separation arm 64 is pressed, it moves relative to the lever portion 76. The follower separation arm 64 further includes a follower member 100 having a follower surface 102 that follows along the cam surfaces 62 of the wall separation features 60 of each sidewall 16 and 18. When the follower separation arm 64 is pushed inward relative to the lever portion 76 with the clamp latching features 56 and 58 received by the latch catch features 92 and, one or both of the cam and follower surfaces 62 and 102 are angled oblique to a plane of the inner surfaces 26 and 28 of the sidewalls 16 and 18 to apply forces against the sidewalls 16 and 18 in opposite directions. The sidewalls 16 and 18 are formed from a resiliently flexible enough material such that they flex in response to the forces and release the detent connection provided by the clamp latching features 56, 58 and the latch catch features 92 and 94.

Figure 4:
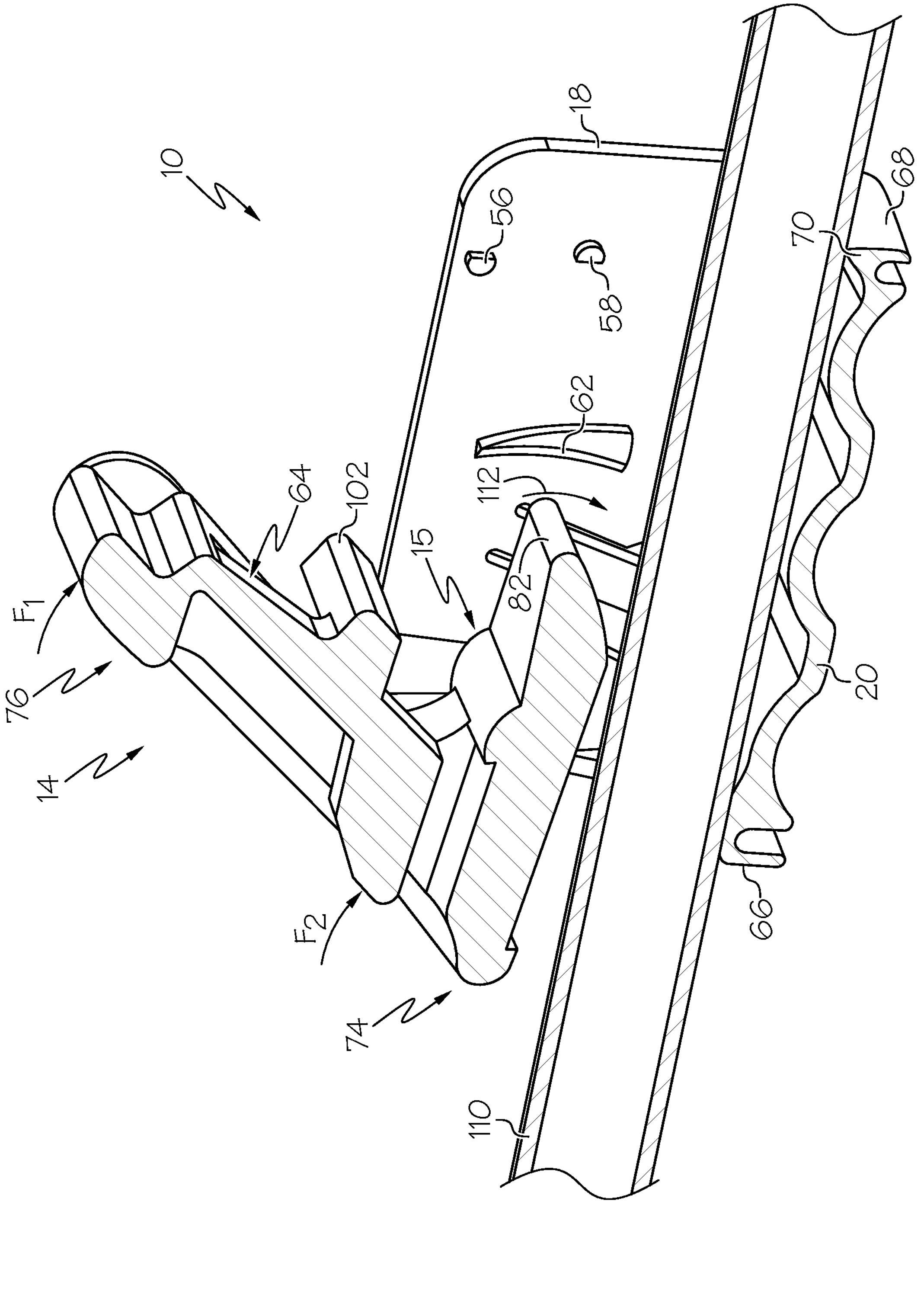
FIG. 4 is a section view of the clamp assembly along line 4-4 of FIG. 1 in an open configuration, according to one or more embodiments shown and described herein.
Figure 5:
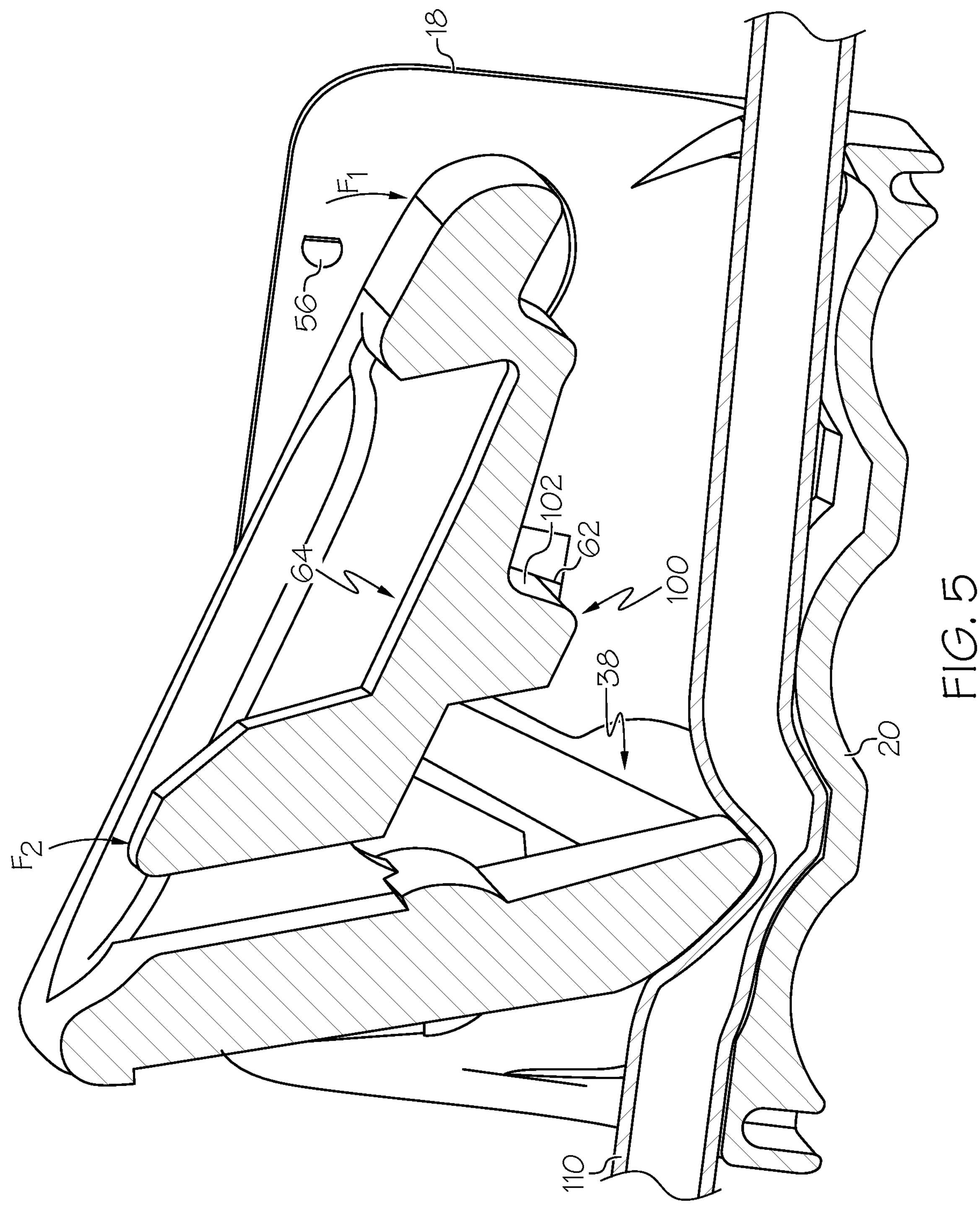
FIG. 5 is a section view of the clamp assembly along line 4-4 of FIG. 1 in a fully closed configuration, according to one or more embodiments shown and described herein.

FIGS. 4 and 5 illustrate operation of the clamp assembly 10 and are section views along lines 4-4 of FIG. 1. FIG. 4 illustrates the clamp assembly 10 in an open configuration. In the open configuration, the latch catch features 92 and 94 (FIG. 3) are removed from the clamp latching features 56 and 58 and the locking lever 14 is free to rotate to the illustrated open position. The pinching edge 82 of the locking lever 14 is farther removed in distance from the bottom 20, which can provide space for insertion of flexible tubing 110. The flexible tubing 110 may be in fluid communication with a system for delivering a fluid to and/or from that system, such as Corning's HYPERStack™ system. The end walls 66 and 68 (FIG. 2) have the reduced height at the center 70 to facilitate insertion of the tubing 110.

Referring also to FIG. 5, because the pivot location 15 is on the pinching portion 74 of the locking lever 14, the motion of the locking lever 14 may be rotation of the pinching portion 74 about the pivot location 15 and the lever portion 76 orbits around the pivot location 15. A manual force $F_1$ may be applied to the lever portion 76, which causes the entire locking lever 14 to rotate with the pinching portion 74 rotating in the direction of arrow 112 toward the tubing 110 and the bottom 20. As the locking lever 14 is rotated, the pinching edge 82 moves toward the bottom 20 thereby decreasing the distance therebetween.

Figure 6:
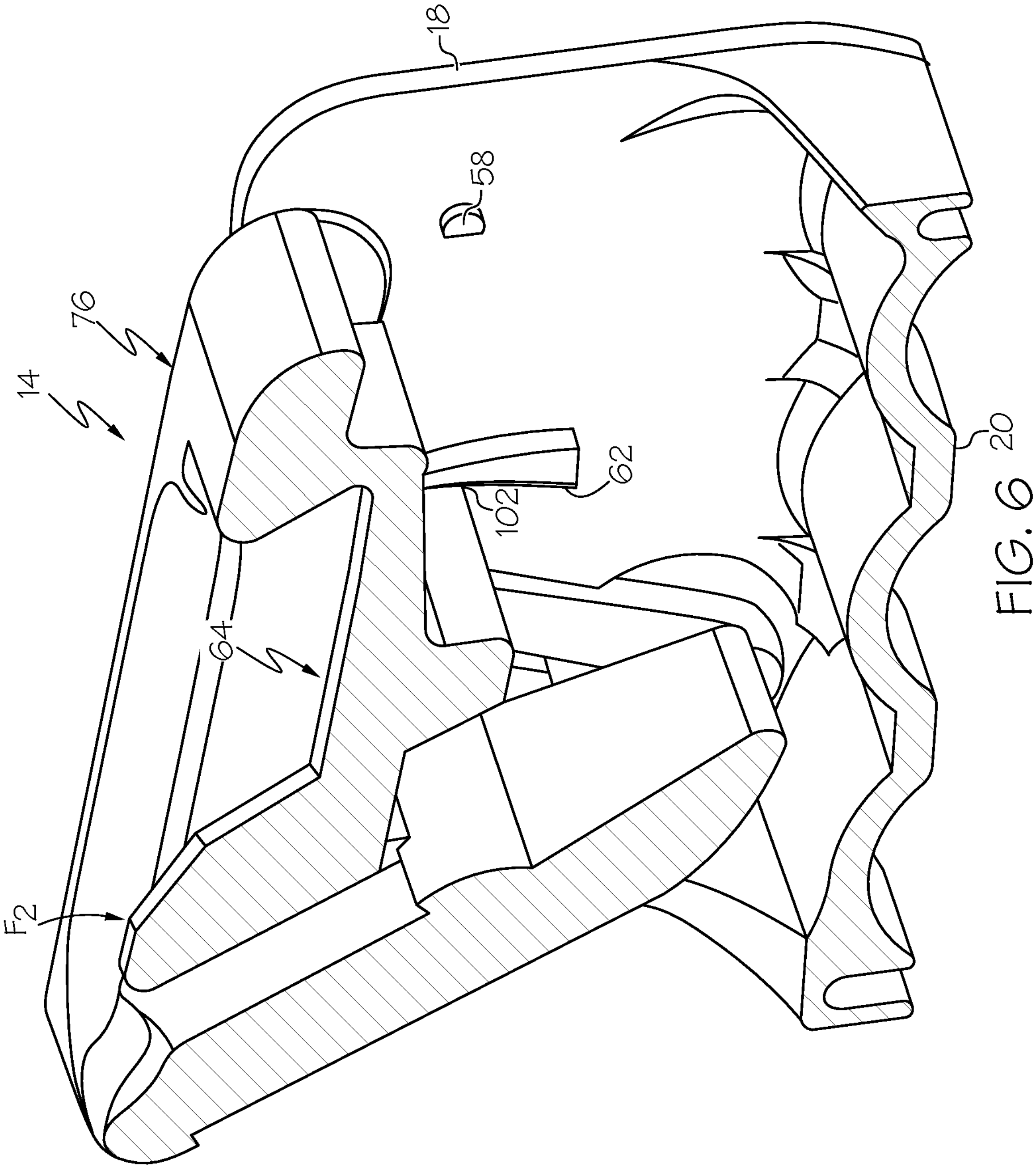
FIG. 6 is a section view of the clamp assembly along line 4-4 of FIG. 1 in a partially closed configuration, according to one or more embodiments shown and described herein.

With continued rotation of the locking lever 14, the pinching edge 82 impinges upon the tubing 110. Referring also to FIG. 6, when the latch catch features 92 and 94 (FIG. 3) reach the clamp latching features 56, the latch catch features 92 and 94 slide upon the clamp latching features 56 associated with each sidewall 16 and 18 and the recessed areas 95 (FIG. 3) receive and mate with the clamp latching features 56 that are farthest from the bottom 20. In this first angular position as shown by FIG. 6, the locking lever 14 is in a partially closed configuration that reduces the inner diameter of the tubing 110, but may not close off the inner diameter of the tubing 110, depending on the wall thickness and size of the tubing 110.

If further clamping and reduced flow rate are desired, e.g., to close off the tubing 110 thereby stopping fluid flow, the follower separation arm 64 can be pressed in the direction of arrow $F_2$ such that it moves relative to the lever portion 76. Such pressure applies a force between the cam and follower surfaces 62 and 102 that forces the sidewalls 16 and 18 apart enough so that the locking lever can rotate to the next clamp latching features 58 positioned closer to the bottom 20 to a second angular position (FIG. 5). As can be appreciated, the latch catch features 92 and 94 and the clamp latching features 56 and 58 cooperate to lock the locking lever at the two different angular positions. The follower separation arm 64 can then be actuated to separate the sidewalls 16 and 18 and release the locking lever 14 so that the locking lever 14 can be moved to the open configuration shown by FIG. 4.

The locking lever 14 may be locked in the closed or partially closed configuration for a selected period of time. Different tubes 110 may be formed of different materials having different levels of resiliency. When the locking lever 14 is moved to the open configuration, it can be the case that the tubing 110 does not fully return to its initial, de-pinched position. If this occurs, the de-pinch features 36 and 38 are provided. The de-pinch features 36 are located adjacent the region of the tubing 110 that is pinched with the locking lever 14 in one or both of the first and second angular positions. The de-pinch features 36 and 38 are configured to resiliently flex such that the projections 48 and 50 (FIGS. 1 and 2) can be manually moved toward one another for a tube de-pinching operation. The projections 48 and 50 are arranged and configured to impinge upon opposite sides of tubing 110 passing through the base member 12 to help return the tubing 110 nearer to its original inner diameter and increase flowrate therethrough.

The above-described apparatuses and methods provide clamp assemblies that contains indexable clap positions, which can enable flow selection by the user. The clamp assemblies include de-pinch features that can be used to open the inner diameter of tubing after the tubing has been pinched closed for a period of time. The geometry of the end walls of the base member have geometries that facilitate passage of tubing hardware through the base member without capturing the hardware.

Embodiments can be described with reference to the following numbered clauses, with preferred features laid out in the dependent clauses:

Clause 1: A clamp assembly for clamping flexible tubing, the clamp assembly comprising: a base member comprising a pair of sidewalls and a bottom that extends between the sidewalls, at least one of the sidewalls including a clamp latching feature extending inward from an inner surface of the at least one of the sidewalls; and a locking lever located between the sidewalls and pivotally connected to the sidewalls at a pivot location such that the locking lever pivots relative to the base member, the locking lever including a lever catch feature configured to cooperatively mate with the clamp latching feature.

Clause 2: The clamp assembly of clause 1 comprising at least two clamp latching features spaced-apart from each other along the inner surface of the at least one of the sidewalls such that the clamp latching features are different distances from the bottom.

Clause 3: The clamp assembly of clause 2, wherein the lever catch feature mates with one of the clamp latching features at a first angular position relative to the base member to lock the locking lever at the first angular position and mates with another of the clamp latching features at a different, second angular position relative to the base member to lock the locking lever at the second angular position.

Clause 4: The clamp assembly of clause 3, wherein the at least two clamp latch features include a first clamp latch feature and a second clamp latch feature, the second clamp latch feature is closer to the bottom of the base member than the first clamp latch feature.

Clause 5: The clamp assembly of any of clauses 1-4, wherein the locking lever includes a lever portion and a pinching portion arranged and configured to impinge on tubing located in the base member, the pivot location located on the pinching portion.

Clause 6: The clamp assembly of any of clauses 1-5, wherein each sidewall has at least two clamp latching features spaced-apart from each other along inner surfaces of the sidewalls such that the clamp latching features of each sidewall are different distances from the bottom.

Clause 7: The clamp assembly of clause 6, wherein the at least two clamp latching features of each sidewall comprise a first post and a second post spaced-apart from the first post.

Clause 8: The clamp assembly of clause 7, wherein the lever catch feature comprises a recess area that is sized and arranged to mate with the first post with the locking lever at a first angular position and a second post with the locking lever at a second, different angular position relative to the base member.

Clause 9: The clamp assembly of any of clauses 1-8, wherein the base member comprises a de-pinching feature that is configured to move inward and impinge upon tubing located in the base member.

Clause 10: The clamp assembly of clause 9, wherein the de-pinching feature comprises a tab that is connected to one of the pair of sidewalls at a mounted end and extends to a free end.

Clause 11: The clamp assembly of clause 10, wherein the de-pinching feature comprises a projection that extends inward from the free end.

Clause 12: The clamp assembly of any of clauses 1-11, wherein the base member comprises an end wall that extends between the pair of sidewalls at an end of the bottom located at a location of ingress and egress for tubing, wherein a height of the end wall is reduced at a center of the end wall compared to at the pair of sidewalls.

Clause 13: A clamp assembly for clamping flexible tubing, the clamp assembly comprising: a base member comprising a pair of sidewalls and a bottom that extends between the sidewalls, at least one of the sidewalls including a clamp latching feature; a locking lever located between the sidewalls and pivotally connected to the sidewalls at a pivot location such that the locking lever pivots relative to the base member, the locking lever including a lever catch feature configured to cooperatively mate with the clamp latching feature; and a de-pinching feature that is configured to move inward and impinge upon tubing located in the base member.

Clause 14: The clamp assembly of clause 13, wherein the de-pinching feature comprises a tab that is connected to one of the pair of sidewalls at a mounted end and extends to a free end.

Clause 15: The clamp assembly of clause 14, wherein the de-pinching feature comprises a projection that extends inward from the free end.

Clause 16: The clamp assembly of any of clauses 13-15, wherein the base member comprises an end wall that extends between the pair of sidewalls at an end of the bottom located at a location of ingress and egress for tubing, wherein a height of the end wall is reduced at a center of the end wall compared to at the pair of sidewalls.

Clause 17: The clamp assembly of any of clauses 13-16, wherein each sidewall has at least two clamp latching features spaced-apart from each other along inner surfaces of the sidewalls such that the clamp latching features of each sidewall are different distances from the bottom.

Clause 18: The clamp assembly of clause 17, wherein the at least two clamp latching features of each sidewall comprise a first post and a second post spaced-apart from the first post.

Clause 19: The clamp assembly of clause 18, wherein the lever catch feature comprises a recess area that is sized and arranged to mate with the first post with the locking lever at a first angular position and a second post with the locking lever at a second, different angular position relative to the base member.

Clause 20: The clamp assembly of any of claims 13-19, wherein the locking lever includes a lever portion and a pinching portion arranged and configured to impinge on tubing located in the base member, the pivot location located on the pinching portion.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A clamp assembly for clamping flexible tubing, the clamp assembly comprising:

a base member comprising a pair of sidewalls and a bottom that extends between the sidewalls, at least one of the sidewalls including at least two clamp latching features extending inward from an inner surface of the at least one of the sidewalls, the at least two clamp latching features being spaced apart from each other along the inner surface of the at least one of the sidewalls; and a locking lever located between the sidewalls and pivotally connected to the sidewalls at a pivot location such that the locking lever pivots relative to the base member, the locking lever including a lever catch feature configured to cooperatively mate with the at least two clamp latching features, wherein the lever catch feature mates with a first one of the at least two clamp latching features at a first angular position relative to the base member, the first angular position corresponding to a first reduction in flow rate through the tubing, and wherein the lever catch feature mates with a second one of the at least two clamp latching features at a different, second angular position relative to the base member, the second angular position corresponding to a greater, second reduction in flow rate through the tubing.

2. The clamp assembly of claim 1, wherein the at least two clamp latching features are different distances from the bottom.

3. The clamp assembly of claim 1, wherein the second one of the at least two clamp latching features is closer to the bottom of the base member than the first one of the at least two clamp latching features.

4. The clamp assembly of claim 1, wherein the locking lever includes a lever portion and a pinching portion arranged and configured to impinge on tubing located in the base member, the pivot location located on the pinching portion.

5. The clamp assembly of claim 1, wherein each sidewall has the at least two clamp latching features spaced-apart from each other along inner surfaces of the sidewalls such that the at least two clamp latching features of each sidewall are different distances from the bottom.

6. The clamp assembly of claim 5, wherein the at least two clamp latching features of each sidewall comprise a first post and a second post spaced-apart from the first post.

7. The clamp assembly of claim 6, wherein the lever catch feature comprises a recess area that is sized and arranged to mate with the first post with the locking lever at a first angular position and a second post with the locking lever at a second, different angular position relative to the base member.

8. The clamp assembly of claim 1, wherein the base member comprises a de-pinching feature that is configured to move inward and impinge upon tubing located in the base member.

9. The clamp assembly of claim 8, wherein the de-pinching feature comprises a tab that is connected to one of the pair of sidewalls at a mounted end and extends to a free end.

10. The clamp assembly of claim 9, wherein the de-pinching feature comprises a projection that extends inward from the free end.

11. The clamp assembly of claim 1, wherein the base member comprises an end wall that extends between the pair of sidewalls at an end of the bottom located at a location of ingress and egress for tubing, wherein a height of the end wall is reduced at a center of the end wall compared to at the pair of sidewalls.

12. A clamp assembly for clamping flexible tubing, the clamp assembly comprising:

a base member comprising a pair of sidewalls and a bottom that extends between the sidewalls, at least one of the sidewalls including a clamp latching feature;

a locking lever located between the sidewalls and pivotally connected to the sidewalls at a pivot location such that the locking lever pivots relative to the base member, the locking lever including a lever catch feature configured to cooperatively mate with the clamp latching feature; and a de-pinching feature that is configured to move inward, contact, and impinge upon tubing located in the base member.

13. The clamp assembly of claim 12, wherein the de-pinching feature comprises a tab that is connected to one of the pair of sidewalls at a mounted end and extends to a free end.

14. The clamp assembly of claim 13, wherein the de-pinching feature comprises a projection that extends inward from the free end.

15. The clamp assembly of claim 12, wherein the base member comprises an end wall that extends between the pair of sidewalls at an end of the bottom located at a location of ingress and egress for tubing, wherein a height of the end wall is reduced at a center of the end wall compared to at the pair of sidewalls.

16. The clamp assembly of claim 12, wherein each sidewall has at least two clamp latching features spaced-apart from each other along inner surfaces of the sidewalls such that the clamp latching features of each sidewall are different distances from the bottom.

17. The clamp assembly of claim 16, wherein the at least two clamp latching features of each sidewall comprise a first post and a second post spaced-apart from the first post.

18. The clamp assembly of claim 17, wherein the lever catch feature comprises a recess area that is sized and arranged to mate with the first post with the locking lever at a first angular position and a second post with the locking lever at a second, different angular position relative to the base member.

19. The clamp assembly of claim 12, wherein the locking lever includes a lever portion and a pinching portion arranged and configured to impinge on tubing located in the base member, the pivot location located on the pinching portion.

* * * * *